United States Patent
Iizuka et al.

(10) Patent No.: US 9,801,580 B2
(45) Date of Patent: Oct. 31, 2017

(54) DRIVING ASSISTANCE DEVICE, DRIVING ASSISTANCE METHOD, INFORMATION-PROVIDING DEVICE, INFORMATION-PROVIDING METHOD, NAVIGATION DEVICE AND NAVIGATION METHOD

(71) Applicant: TOYOTA JIDOSHA KABUSHIKI KAISHA, Toyota-shi, Aichi (JP)

(72) Inventors: Hisashi Iizuka, Susono (JP); Hirotaka Kaji, Hadano (JP); Hirokazu Kikuchi, Hadano (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 56 days.

(21) Appl. No.: 14/777,138

(22) PCT Filed: Mar. 22, 2013

(86) PCT No.: PCT/JP2013/058364
§ 371 (c)(1),
(2) Date: Sep. 15, 2015

(87) PCT Pub. No.: WO2014/147828
PCT Pub. Date: Sep. 25, 2014

(65) Prior Publication Data
US 2016/0029940 A1 Feb. 4, 2016

(51) Int. Cl.
*A61B 5/18* (2006.01)
*A61B 5/0245* (2006.01)
*A61B 5/0476* (2006.01)
*G08G 1/16* (2006.01)
*B60K 28/00* (2006.01)
*B60W 50/12* (2012.01)
*A61B 3/11* (2006.01)
(Continued)

(52) U.S. Cl.
CPC ............... *A61B 5/18* (2013.01); *A61B 3/112* (2013.01); *A61B 5/0205* (2013.01);
(Continued)

(58) Field of Classification Search
CPC ......... A61B 3/112; A61B 5/18; A61B 5/0205; A61B 5/0245; A61B 5/0476;
(Continued)

(56) References Cited

U.S. PATENT DOCUMENTS

2003/0043045 A1    3/2003  Yasushi et al.
2008/0180257 A1*   7/2008  Omi ..................... B60K 28/06
                                                         340/575
(Continued)

FOREIGN PATENT DOCUMENTS

CN    101980660 B     1/2013
DE    102011109564 A1  2/2013
(Continued)

*Primary Examiner* — Calvin Cheung
(74) *Attorney, Agent, or Firm* — Sughrue Mion, PLLC

(57) ABSTRACT

A heartbeat sensor obtains a heartbeat of a driver. A concentration level computing unit estimates a concentration level of the driver at a time later than a timing of obtaining the heartbeat by the heartbeat sensor, on the basis of the heartbeat obtained by the heartbeat sensor. A state determining unit controls driving assistance for a vehicle on the basis of a comparison of the concentration level of the driver estimated by the concentration level computing unit with a target concentration level of the driver that is set in association with a position or an environment in which the vehicle driven by the driver is predicted to travel.

8 Claims, 14 Drawing Sheets

(51) Int. Cl.
  *A61B 5/0205* (2006.01)
  *A61B 5/00* (2006.01)
  *B60W 40/08* (2012.01)
  *B60W 50/00* (2006.01)

(52) U.S. Cl.
  CPC .......... *A61B 5/0245* (2013.01); *A61B 5/0476* (2013.01); *A61B 5/7275* (2013.01); *A61B 5/7278* (2013.01); *A61B 5/742* (2013.01); *B60K 28/00* (2013.01); *B60W 40/08* (2013.01); *B60W 50/12* (2013.01); *G08G 1/16* (2013.01); *B60W 2040/0872* (2013.01); *B60W 2050/0064* (2013.01); *B60W 2540/22* (2013.01); *Y02T 10/84* (2013.01)

(58) Field of Classification Search
  CPC ..... A61B 5/7275; A61B 5/7278; A61B 5/742; B60K 28/00; B60W 40/08; B60W 50/12; G08G 1/16
  See application file for complete search history.

(56) References Cited

U.S. PATENT DOCUMENTS

| | | |
|---|---|---|
| 2010/0234747 A1 | 9/2010 | Hatakeyama |
| 2010/0241021 A1 | 9/2010 | Morikawa et al. |
| 2011/0224875 A1* | 9/2011 | Cuddihy ................ B60K 28/06 701/42 |
| 2011/0313259 A1 | 12/2011 | Hatakeyama et al. |
| 2012/0095358 A1 | 4/2012 | Matsunaga et al. |
| 2012/0256749 A1* | 10/2012 | Rao ..................... A61B 5/0022 340/573.1 |
| 2013/0231800 A1* | 9/2013 | Ricci ........................ G06F 9/54 701/1 |
| 2014/0135598 A1 | 5/2014 | Weidl et al. |
| 2016/0001781 A1* | 1/2016 | Fung .................... G06F 19/345 701/36 |

FOREIGN PATENT DOCUMENTS

| | | |
|---|---|---|
| JP | 6-255520 A | 9/1994 |
| JP | 2003-61939 A | 3/2003 |
| JP | 2007-64797 A | 3/2007 |
| JP | 2008-15561 A | 1/2008 |
| JP | 2009-39167 A | 2/2009 |
| JP | 2009-73465 A | 4/2009 |
| JP | 2012-81194 A | 4/2012 |
| JP | 2012-112853 A | 6/2012 |
| JP | 2014-202733 A | 10/2014 |
| WO | 2007/090896 A1 | 8/2007 |
| WO | 2012/144948 A1 | 10/2012 |

* cited by examiner

DRIVING ASSISTANCE DEVICE, DRIVING ASSISTANCE METHOD, INFORMATION-PROVIDING DEVICE, INFORMATION-PROVIDING METHOD, NAVIGATION DEVICE AND NAVIGATION METHOD

CROSS REFERENCE TO RELATED APPLICATIONS

This application is a National Stage of International Application No. PCT/JP2013/058364, filed on Mar. 22, 2013, the contents of all of which are incorporated herein by reference in their entirety.

TECHNICAL FIELD

One embodiment of the present invention relates to a driving assistance device, a driving assistance method, an information-providing device, an information-providing method, a navigation device, and a navigation method.

BACKGROUND ART

Recently, there has been suggested a device that detects a decrease and the like in the concentration level of a driver who drives a vehicle and that informs the driver of the decrease in the concentration level. For example, in Patent Literature 1, there is disclosed a device that predicts the future occurrence of sleepiness, fatigue, and the like of a driver until the driver reaches a predetermined position on the basis of biometric information such as heart rate, respiratory rate, blink speed, and the like of the driver of a vehicle and on the basis of load exerted on the driver by a road until the vehicle reaches the predetermined position. The device of Patent Literature 1 calls to the attention of the driver in advance on the basis of the sleepiness of the driver at the predetermined position.

CITATION LIST

Patent Literature

[Patent Literature 1] Japanese Unexamined Patent Application Publication No. 2003-61939

SUMMARY OF INVENTION

Technical Problem

In the above technology, however, attention of the driver may be called even when calling attention of the driver and the like are not necessarily required. Thus, the driver may feel inconvenienced.

One embodiment of the present invention is devised with consideration of the problem above, and an object thereof is to provide a driving assistance device, a driving assistance method, an information-providing device, an information-providing method, a navigation device, and a navigation method, in which a driver feels less inconvenienced by performing driving assistance that is more appropriate for a situation where a vehicle is traveling.

Solution to Problem

According to an aspect of the present invention, there is provided a driving assistance device including: a biometric information obtaining unit configured to obtain biometric information of a driver; a driver state estimating unit configured to estimate, on the basis of the biometric information obtained by the biometric information obtaining unit, a state of the driver at a time later than a timing of obtaining the biometric information by the biometric information obtaining unit; and a control unit configured to control driving assistance of a vehicle on the basis of a comparison of the state of the driver estimated by the driver state estimating unit with a condition for the state of the driver that is set in association with any one of a position and an environment in which the vehicle driven by the driver is predicted to travel.

According to this configuration, the biometric information obtaining unit obtains the biometric information of the driver. The driver state estimating unit, on the basis of the biometric information obtained by the biometric information obtaining unit, estimates the state of the driver at a time later than the timing of obtaining the biometric information by the biometric information obtaining unit. The control unit controls the driving assistance of the vehicle on the basis of the comparison of the state of the driver estimated by the driver state estimating unit with the condition for the state of the driver that is set in association with any one of the position and the environment in which the vehicle driven by the driver is predicted to travel. Accordingly, current driving assistance is controlled on the basis of the comparison of the future state of the driver based on the actual obtained biometric information with the condition for the state of the driver that is obtained in the position or the environment in which the vehicle travels in the future. Thus, driving assistance is performed more appropriately for the situation in which the driver performs driving in the position or the environment, and the possibility of causing the driver to feel inconvenienced can be reduced.

The control unit may promote the driving assistance as the degree to which the state of the driver estimated by the driver state estimating unit does not satisfy the condition for the state of the driver that is set in association with any one of the position and the environment in which the vehicle driven by the driver is predicted to travel is greater.

According to this configuration, the control unit promotes the driving assistance as the degree to which the state of the driver estimated by the driver state estimating unit does not satisfy the condition for the state of the driver that is set in association with any one of the position and the environment in which the vehicle driven by the driver is predicted to travel is greater. Accordingly, driving assistance is promoted as the state of the driver is worse in the situation in which the driver performs driving in the position or the environment. Thus, driving assistance is performed more appropriately for the state of the driver and the condition corresponding to the position and the environment, and the possibility of causing the driver to feel inconvenienced can be reduced.

The control unit may control the driving assistance to be initiated when the state of the driver estimated by the driver state estimating unit does not satisfy the condition for the state of the driver that is set in association with any one of the position and the environment in which the vehicle driven by the driver is predicted to travel.

According to this configuration, the control unit initiates the driving assistance when the state of the driver estimated by the driver state estimating unit does not satisfy the condition for the state of the driver that is set in association with any one of the position and the environment in which the vehicle driven by the driver is predicted to travel. Thus, driving assistance is performed for the state of the driver and the condition corresponding to the position and the environment when necessary, and the possibility of causing the driver to feel inconvenienced can be reduced.

The state of the driver may be a concentration level of the driver.

According to this configuration, the state of the driver is the concentration level of the driver. Accordingly, current driving assistance is controlled on the basis of the comparison of the future concentration level of the driver based on the actual obtained biometric information with the condition for the concentration level of the driver that is obtained in the position or the environment in which the vehicle travels in the future. Thus, driving assistance is performed more appropriately for the concentration level that is required in the situation in which the driver performs driving in the position or the environment, and the possibility of causing the driver to feel inconvenienced can be reduced.

The driver state estimating unit, on the basis of the biometric information obtained by the biometric information obtaining unit, may estimate a tendency of the concentration level of the driver to decrease over time.

According to this configuration, the driver state estimating unit, on the basis of the biometric information obtained by the biometric information obtaining unit, estimates a tendency of the concentration level of the driver to decrease over time. Accordingly, the concentration level of the driver when the vehicle actually travels in the position or the environment can be estimated more accurately, and driving assistance can be performed more appropriately for the concentration level of the driver.

The driver state estimating unit, on the basis of the biometric information obtained by the biometric information obtaining unit, may estimate a tendency of the concentration level of the driver to decrease over time by estimating a degree of accumulation of the concentration level of the driver over time.

According to this configuration, the driver state estimating unit, on the basis of the biometric information obtained by the biometric information obtaining unit, estimates a tendency of the concentration level of the driver to decrease over time by estimating a degree of accumulation of the concentration level of the driver over time. The degree of accumulation of the concentration level over time is unlikely to be affected by temporary variation of the concentration level of the driver. Therefore, a tendency of the concentration level of the driver to decrease over time can be estimated more accurately regardless of temporary variation of the concentration level of the driver by estimating the degree of accumulation of the concentration level over time.

The driver state estimating unit, on the basis of the biometric information obtained by the biometric information obtaining unit, may estimate a period of time until the degree of accumulation of the concentration level of the driver over time is saturated and may estimate a tendency of the concentration level of the driver to decrease over time on the basis of the time period until the degree of accumulation is saturated.

According to this configuration, the driver state estimating unit, on the basis of the biometric information obtained by the biometric information obtaining unit, estimates a period of time until the degree of accumulation of the concentration level of the driver over time is saturated and estimates a tendency of the concentration level of the driver to decrease over time on the basis of the time period until the degree of accumulation is saturated. The period of time until the degree of accumulation of the concentration level of the driver over time is saturated is unlikely to be affected by temporary variation of the concentration level of the driver. Therefore, a tendency of the concentration level of the driver to decrease over time can be estimated more accurately regardless of temporary variation of the concentration level of the driver by estimating the period of time until the degree of accumulation of the concentration level of the driver over time is saturated.

The control unit, on the basis of the biometric information obtained by the biometric information obtaining unit, may associate the state of the driver estimated at the timing of obtaining the biometric information by the biometric information obtaining unit with any one of the position and the environment in which the vehicle driven by the driver travels and may record the association.

According to this configuration, the control unit, on the basis of the biometric information obtained by the biometric information obtaining unit, associates the state of the driver estimated at the timing of obtaining the biometric information by the biometric information obtaining unit with any one of the position and the environment in which the vehicle driven by the driver travels and records the association. Accordingly, the state of the driver when the vehicle travels in the position or the environment can be correlated with the position or the environment.

The condition for the state of the driver that is set in association with any one of the position and the environment in which the vehicle driven by the driver is predicted to travel may be set on the basis of the state of the driver that is recorded in association with any one of the position and the environment in which the vehicle driven by the driver travels.

According to this configuration, the condition for the state of the driver that is set in association with any one of the position and the environment in which the vehicle driven by the driver is predicted to travel is set on the basis of the state of the driver that is recorded in association with any one of the position and the environment in which the vehicle driven by the driver travels. Therefore, the condition for the state of the driver corresponds to the state of the driver when the vehicle travels in the position or the environment, and the condition can be set more realistically.

The control unit may perform the driving assistance that is set in association with any one of the position and the environment in which the vehicle driven by the driver is predicted to travel.

According to this configuration, the control unit performs the driving assistance that is set in association with any one of the position and the environment in which the vehicle driven by the driver is predicted to travel. Thus, it is possible to perform driving assistance that is more appropriate for the position or the environment in which the vehicle travels.

The control unit may call attention of the driver when the state of the driver estimated by the driver state estimating unit is below a first threshold and may perform the driving assistance of intervening in a driving operation by the driver when the state of the driver estimated by the driver state estimating unit is below a second threshold that is lower than the first threshold.

According to this configuration, the control unit calls to the attention of the driver when the state of the driver estimated by the driver state estimating unit is below a first threshold and performs the driving assistance of intervening in a driving operation by the driver when the state of the driver estimated by the driver state estimating unit is below a second threshold that is lower than the first threshold. Accordingly, the concentration level and the like required for the driver to drive the vehicle can be reduced. In addition, an inconvenient feeling of the driver can be reduced because assistance that the driver needs is provided.

According to another aspect of the present invention, there is provided a driving assistance method including a biometric information obtaining step of obtaining biometric information of a driver, a driver state estimating step of estimating, on the basis of the biometric information obtained through the biometric information obtaining step, a state of the driver at a time later than a timing of obtaining the biometric information through the biometric information obtaining step, and a control step of controlling driving assistance of a vehicle on the basis of a comparison of the state of the driver estimated through the driver state estimating step with a condition for the state of the driver that is set in association with any one of a position and an environment in which the vehicle driven by the driver is predicted to travel.

According to still another aspect of the present invention, there is provided an information-providing device including a biometric information obtaining unit configured to obtain biometric information of a driver, a driver state estimating unit configured to estimate, on the basis of the biometric information obtained by the biometric information obtaining unit, a state of the driver at a time later than a timing of obtaining the biometric information by the biometric information obtaining unit, and a reporting unit configured to call attention of the driver of a vehicle on the basis of a comparison of the state of the driver estimated by the driver state estimating unit with a condition for the state of the driver that is set in association with any one of a position and an environment in which the vehicle driven by the driver is predicted to travel.

According to this configuration, the biometric information obtaining unit obtains the biometric information of the driver. The driver state estimating unit, on the basis of the biometric information obtained by the biometric information obtaining unit, estimates the state of the driver at a time later than the timing of obtaining the biometric information by the biometric information obtaining unit. The reporting unit calls to the attention of the driver of the vehicle on the basis of the comparison of the state of the driver estimated by the driver state estimating unit with the condition for the state of the driver that is set in association with any one of the position and the environment in which the vehicle driven by the driver is predicted to travel. Accordingly, attention of the driver is currently called on the basis of the comparison of the future state of the driver based on the actual obtained biometric information with the condition for the state of the driver that is obtained in the position or the environment in which the vehicle travels in the future. Thus, attention is called more appropriately for the situation in which the driver performs driving in the position or the environment, and the possibility of causing the driver to feel inconvenienced can be reduced.

According to still another aspect of the present invention, there is provided an information-providing method including a biometric information obtaining step of obtaining biometric information of a driver, a driver state estimating step of estimating, on the basis of the biometric information obtained through the biometric information obtaining step, a state of the driver at a time later than a timing of obtaining the biometric information through the biometric information obtaining step, and a reporting step of calling attention of the driver of a vehicle on the basis of a comparison of the state of the driver estimated through the driver state estimating step with a condition for the state of the driver that is set in association with any one of a position and an environment in which the vehicle driven by the driver is predicted to travel.

According to still another aspect of the present invention, there is provided a navigation device including a biometric information obtaining unit configured to obtain biometric information of a driver, a driver state estimating unit configured to estimate, on the basis of the biometric information obtained by the biometric information obtaining unit, a state of the driver at a time later than a timing of obtaining the biometric information by the biometric information obtaining unit, and a course selecting unit configured to select a course to guide the driver from a plurality of courses on the basis of a comparison of the state of the driver estimated by the driver state estimating unit with a condition for the state of the driver that is set in association with any one of a position and an environment in which the vehicle driven by the driver is predicted to travel in the plurality of courses.

According to this configuration, the biometric information obtaining unit obtains the biometric information of the driver. The driver state estimating unit, on the basis of the biometric information obtained by the biometric information obtaining unit, estimates the state of the driver at a time later than the timing of obtaining the biometric information by the biometric information obtaining unit. The course selecting unit selects the course to guide the driver from the plurality of courses on the basis of the comparison of the state of the driver estimated by the driver state estimating unit with the condition for the state of the driver that is set in association with any one of the position and the environment in which the vehicle driven by the driver is predicted to travel in the plurality of courses. Accordingly, the course to guide the driver is selected on the basis of the comparison of the future state of the driver based on the actual obtained biometric information with the condition for the state of the driver obtained in the position or the environment in which the vehicle is predicted to travel in the future in the multiple courses. Thus, the course that is more appropriate for the situation in which the driver performs driving in the position or the environment is guided, and the possibility of causing the driver to feel inconvenienced can be reduced.

According to still another aspect of the present invention, there is provided a navigation method including a biometric information obtaining step of obtaining biometric information of a driver, a driver state estimating step of estimating, on the basis of the biometric information obtained through the biometric information obtaining step, a state of the driver at a time later than a timing of obtaining the biometric information through the biometric information obtaining step, and a course selecting step of selecting the course to guide the driver from a plurality of courses on the basis of a comparison of the state of the driver estimated through the driver state estimating step with a condition for the state of the driver that is set in association with any one of a position and an environment in which the vehicle driven by the driver is predicted to travel in the plurality of courses.

Advantageous Effects of Invention

According to the driving assistance device, the driving assistance method, the information-providing device, the information-providing method, the navigation device, and the navigation method of one embodiment of the present invention, a driver feels less inconvenienced by performing driving assistance that is more appropriate for a situation where a vehicle is traveling.

DESCRIPTION OF EMBODIMENTS

Figure 1:
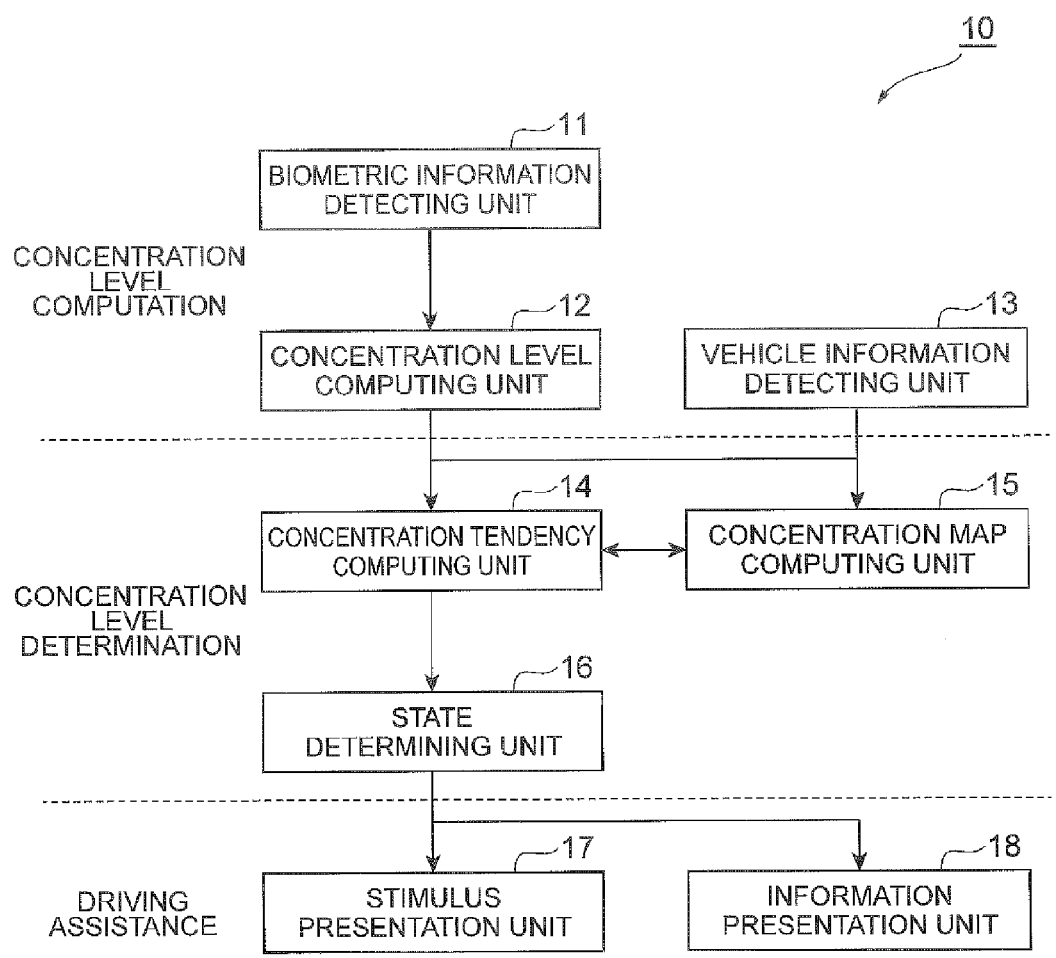
FIG. 1 is a block diagram illustrating a basic configuration of a driving assistance system according to an embodiment.

Examples of a driving assistance device, an information-providing device, and a navigation device according to one embodiment of the present invention will be described with reference to the drawings. First, a basic configuration of the driving assistance device and the like of the present embodiment will be described. As illustrated in FIG. 1, as a basic configuration, a driving assistance system 10 of the present embodiment is provided with a biometric information detecting unit 11, a concentration level computing unit 12, a vehicle information detecting unit 13, a concentration tendency computing unit 14, a concentration map computing unit 15, a state determining unit 16, a stimulus presentation unit 17, and an information presentation unit 18.

The biometric information detecting unit 11 obtains biometric information of a subject such as a driver. The biometric information detecting unit 11 estimates the concentration level of a driver by estimating the state of brainwaves of the driver and the like from biometric information other than brainwaves. Accordingly, the concentration level of a driver can be estimated without detecting brainwaves that are comparatively difficult to detect. Brainwaves may be measured to correct estimation made by other indexes, with the purpose of improving the accuracy of the estimation. In this case, the brainwaves of a driver are required to be measured at one or more locations.

The biometric information detecting unit 11 obtains biometric information that represents pulsation of a heart such as a heartbeat and a pulse wave required in estimating the concentration level of a driver. A method for obtaining biometric information may be any of a contact type and a contactless type. The biometric information detecting unit 11 can be either a physiological index detecting device, a piezoelectric element, an acceleration sensor, or the like installed in a seat or a steering wheel of a vehicle. The biometric information detecting unit 11 may use other biometric information such as a breath and a blink so as to estimate the concentration level of a driver. The biometric information detecting device for a heartbeat or a pulse wave may measure a potential difference thereof or may measure a potential difference from the amount of transmission of a light ray or the amount of reflection thereof.

As will be described below, the biometric information detecting unit 11 can be a heartbeat sensor or the like that is attached to the body of a driver even when the driver is not in the vehicle. As such, in the present embodiment, the concentration level of a driver can be estimated independently of environmental noise by not using the speed, the acceleration, and the like of the vehicle in estimating the concentration level of the driver. In addition, the state of a driver before the driver enters the vehicle can be observed and be reflected in estimating a concentration level by providing the biometric information detecting unit 11 as a heartbeat sensor or the like that is attached to the body of the driver even when the driver is not in the vehicle because the biometric information detecting unit 11 is independent of the vehicle.

The concentration level computing unit 12 computes the amount of features required in estimating, for example, a $\theta$ wave content ratio which indicates the state of the brainwaves of a driver from the biometric information obtained from the biometric information detecting unit 11. Then, the concentration level computing unit 12 estimates the concentration level of a driver. For a heartbeat, the interval between characteristic sharp waves which are called R waves can be used as the amount of features obtained from pulsation. For a pulse wave, the interval between peak values can be used as the amount of features obtained from pulsation. The heart rate of a driver can be computed from the number of intervals per unit time. An instantaneous heart rate can be computed by dividing 60 seconds by the interval of one waveform.

The concentration level computing unit 12, for the fluctuation of a heartbeat, may use a distribution, a standard deviation, and a coefficient of variation of the intervals of pulsation. In addition, the concentration level computing unit 12 may compute the amount of the fluctuation by performing frequency conversion on the intervals of pulsation per unit time. The concentration level computing unit 12, for brainwaves, can compute the amount of features of brainwaves which is a power spectrum of a $\beta$ wave, an $\alpha$ wave, a $\theta$ wave, a $\delta$ wave, a $\sigma$ wave, and an arbitrary frequency band of brainwaves.

The vehicle information detecting unit 13 obtains information related to the latitude and the longitude of the vehicle from a global positioning system (GPS) so as to correlate map information with a concentration level. In addition, the vehicle information detecting unit 13 obtains map information such as the curvature, the width, the gradient, the speed limit, and the amount of traffic of the road on which the vehicle travels, from the map information that corresponds to the latitude and the longitude of the vehicle. The vehicle information detecting unit 13 can obtain signals related to the state of the vehicle such as the extent of braking, the degree to which an accelerator is opened, and a steering angle of the vehicle from a controller area network (CAN).

The concentration tendency computing unit 14 computes a temporal trend in concentration level from the θ wave content ratio obtained by the concentration level computing unit 12. The concentration tendency computing unit 14 computes a tendency of the concentration level of a driver to be attenuated from a temporal trend in the θ wave content ratio. Accordingly, in the present embodiment, it is possible to report to a driver and perform driving assistance before driving becomes inappropriate for the driver by predicting the tendency of the concentration level of the driver to decrease.

As will be described below, the concentration tendency computing unit 14 measures the cumulative number of concentration levels over time. The concentration tendency computing unit 14 formalizes a trend in concentration level from the period of time until the cumulative number of concentration levels reaches an arbitrary threshold. The concentration tendency computing unit 14 can accurately estimate a temporal trend in concentration level by estimating the period of time until the cumulative number of concentration levels is saturated. In addition, the concentration tendency computing unit 14 can estimate a temporal trend in concentration level in accordance with individual drivers. As such, in the present embodiment, even when the tendency of the concentration level of a driver to decrease is different for each day, a trend in concentration level can be measured with the cumulative number of concentration levels for each individual driver independently of an absolute value that is likely to vary.

The concentration map computing unit 15 collectively stores the θ wave content ratio obtained by the concentration level computing unit 12 and the map information obtained by the vehicle information detecting unit 13 such as the curvature, the width, the gradient, the speed limit, and the amount of traffic of the road. In the present embodiment, it is possible to obtain a change in the concentration level of a driver in the situation of the road on which the vehicle has actually traveled. Meanwhile, in the present embodiment, it is possible to estimate the concentration level of a driver in a situation similar to the situation of the road on which the vehicle has actually traveled. Accordingly, it is possible to estimate a concentration level required for a driver to drive on a certain road, even when the road is unknown, by comparing the concentration level of the driver and the data obtained from the GPS and the map information.

The state determining unit 16 determines whether it is necessary to report to a driver or to intervene in a driving operation from a change in concentration level computed by the concentration tendency computing unit 14.

The stimulus presentation unit 17 performs stimulus presentation so as to maintain or improve the concentration level of a driver when the state determining unit 16 determines that the concentration level of a driver exceeds a certain threshold or when the state determining unit 16 determines that the amount of change in the concentration level of a driver exceeds a certain threshold. The stimulus presentation unit 17 may include a map on which stimulus presentation methods associated with individual situations are recorded so as to determine the stimulus presentation method. The stimulus presentation unit 17 may use physical stimuli. The stimulating presentation unit 17 can use, for example, light, sound, vibration, heating, cold wind, smell, and video.

The information display unit 18 presents the result of estimation of the concentration level of a driver to the driver. In addition, the information display unit 18 performs driving assistance for a driver depending on the concentration level of the driver. The information display unit 18, for example, can perform, in order, driving assistance of maintaining a lane, driving assistance of maintaining a vehicle speed and the distance between vehicles, driving assistance of avoiding collision and reducing the damage of collision, driving assistance of guiding the course of the vehicle, and driving assistance of causing the vehicle to avoid obstacles in response to a decrease in the concentration level of a driver.

In the present embodiment, a concentration level necessary for driving can be decreased by performing driving assistance that intervenes in a driving operation by a driver, such as driving assistance of maintaining a vehicle speed and the distance between vehicles, and the driver can drive with a low concentration level. In addition, inconvenience due to driving assistance can be reduced because the driving assistance that the driver actually needs is provided.

Figure 2:
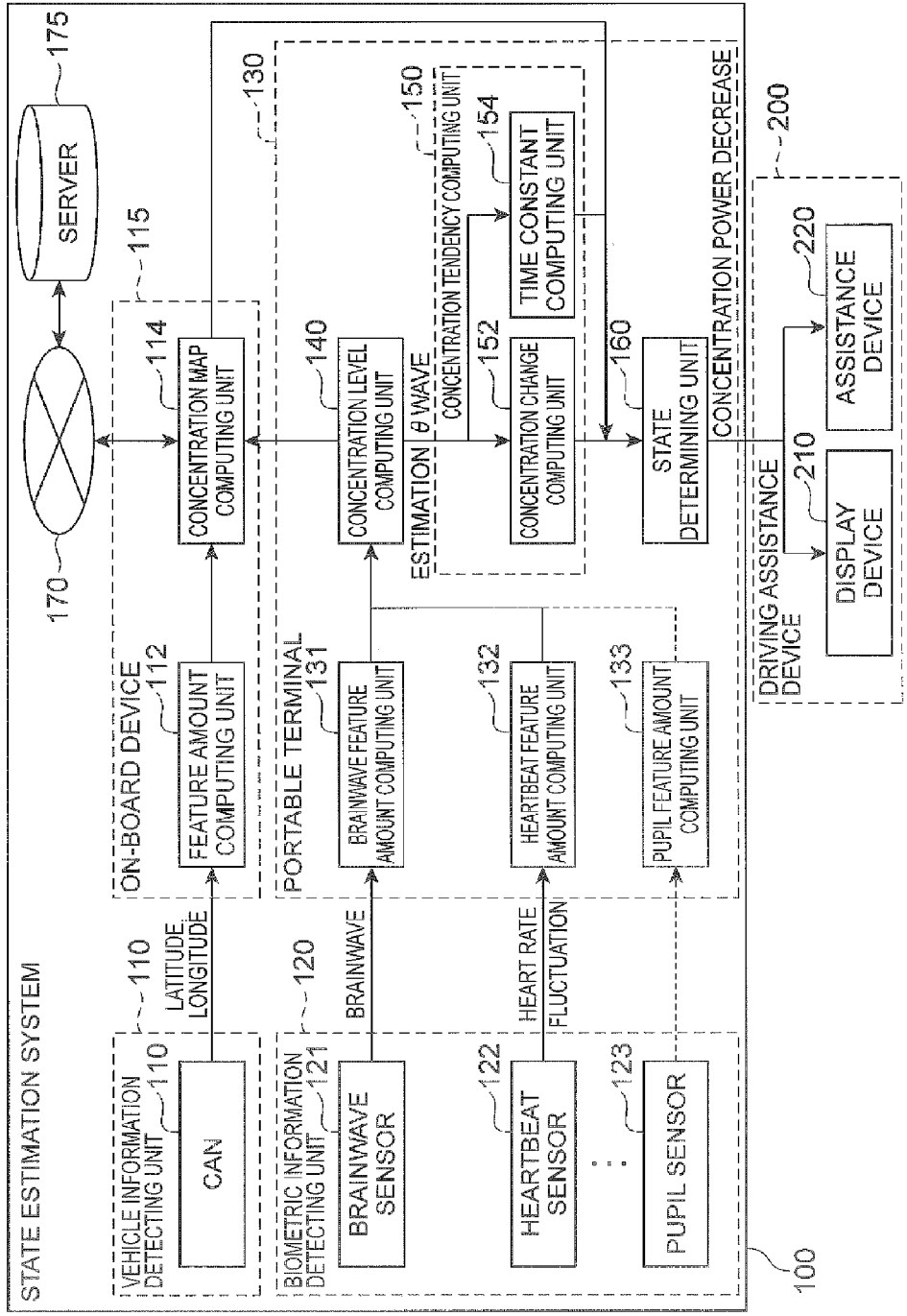
FIG. 2 is a block diagram illustrating in detail a state estimation system and a driving assistance device according to the embodiment.

Hereinafter, an actual hardware configuration of the driving assistance system of the present embodiment will be described. As illustrated in FIG. 2, in a state estimation system 100, a vehicle information detecting unit 110 and a feature amount computing unit 112 that correspond to the vehicle information detecting unit 13 of FIG. 1 are configured as a device mounted in the vehicle.

An on-board device 115 includes the feature amount computing unit 112 and a concentration map computing unit 114 that corresponds to the concentration map computing unit 15 of FIG. 1. The concentration map computing unit 114 communicates with a server 175 outside the vehicle through a network 170. The server 175, for each driver, stores a concentration map on which the position, the shape, and the environment of each traveled road are correlated with the concentration level at that time.

Figure 3:
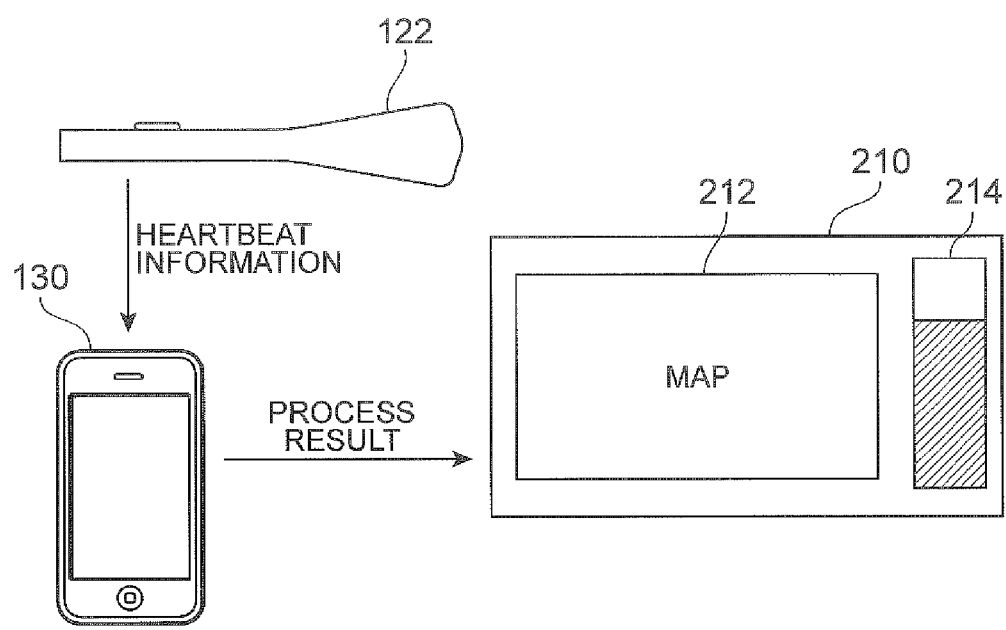
FIG. 3 is a diagram illustrating an example of hardware that constitutes the state estimation system and the driving assistance device of FIG. 2.

A display device 210 and an assistance device 220 that correspond to the stimulus presentation unit 17 and the information presentation unit 18 of FIG. 1 are mounted in a driving device 200 of the vehicle. The display device 210 is, for example, a display in a navigation system. As illustrated in FIG. 3, the display device 210 displays a map 212 and a concentration power 214 as a graph. As such, the display device 210 can display the information related to the concentration level of a driver to the driver and can lead the driver to control the course of the vehicle in a specific direction. The assistance device 200 exerts predetermined reaction or vibration on the steering wheel, the accelerator pedal, and the brake pedal and leads a driving operation by a driver. The assistance device 220 may be a type that controls the steering angle, the degree to which the accelerator is opened, and the extent of braking of the vehicle independently of a driving operation by a driver.

Meanwhile, a brainwave sensor 121, a heartbeat sensor 122, a pupil sensor 123, and the like of a biometric information detecting unit 120 that corresponds to the biometric information detecting unit 11 of FIG. 1 can be configured like, for example, the heartbeat sensor 122 and the like as illustrated in FIG. 3 that are mounted on a driver even when the driver is not in the vehicle. The heartbeat sensor 122 can be configured as, for example, a wireless electrocardiographic sensor that measures the heartbeat of a driver with a disposable electrode installed in the chest portion of the driver and that transmits the measurement result wirelessly.

A brainwave feature amount computing unit 131, a heartbeat feature amount computing unit 132, a pupil feature amount computing unit 133, and a concentration level computing unit 140 of FIG. 2 that correspond to the concentration level computing unit 12 of FIG. 1 can be stored in a portable terminal 130 that a driver carries as illustrated in FIG. 2 and FIG. 3. In addition, a concentration change computing unit 152 and a time constant computing unit 154 of a concentration tendency computing unit 150 of FIG. 2 that corresponds to the concentration tendency computing unit 14 of FIG. 1 can be stored in the portable terminal 130 that a driver carries as illustrated in FIG. 2 and FIG. 3. Furthermore, a state determining unit 160 of FIG. 2 that corresponds to the state determining unit 16 of FIG. 1 can be stored in the portable terminal 130 that a driver carries as illustrated in FIG. 2 and FIG. 3.

In the present embodiment, as such, since the units estimating the tendency of the concentration level of a driver are stored in the portable terminal that the driver carries even outside the vehicle, the concentration level of the driver can be estimated on the basis of data that is obtained under different conditions over a longer period of time, and the accuracy of estimation of a concentration level can be improved. When a driver is not in the vehicle, the concentration level of the driver can be estimated by each configuration in the portable terminal 130 while the heartbeat sensor 122 and the like are mounted on the driver. Meanwhile, when a driver is in the vehicle, the driver can receive driving assistance that will be described below by connecting the portable terminal 130 to the on-board device 115 or the driving assistance device 200 in the vehicle via a wired or wireless connection.

The display device 210 is not limited to an on-board display. A display of the portable terminal 130 that a driver carries can be configured as the display device 210 of the present embodiment. In this case, even when the driver is in the vehicle, the display of the portable terminal 130 can be configured as the display device 210 of the present embodiment.

Hereinafter, operations of the state estimation system 100 and the driving assistance device 200 of the present embodiment will be described. In the example below, a description will be mainly provided of an aspect in which the heartbeat of a driver is used to estimate a θ wave of the brainwaves of the driver and the concentration level of the driver. It is known that a characteristic sharp wave such as a θ wave called Fmθ is generated in the frontal lobes when a human being concentrates. In the technology of the related art, the concentration level of a driver is estimated from the state quantities of the vehicle, environmental information, the situation that the driver observes, and the like. In the estimation with these factors, errors occur due to the environment such as steering deviation caused by ruts. However, in the present embodiment, the concentration level of a human being can be estimated independently of interruption by using biometric information that is the internal information of a human being.

Figure 4:
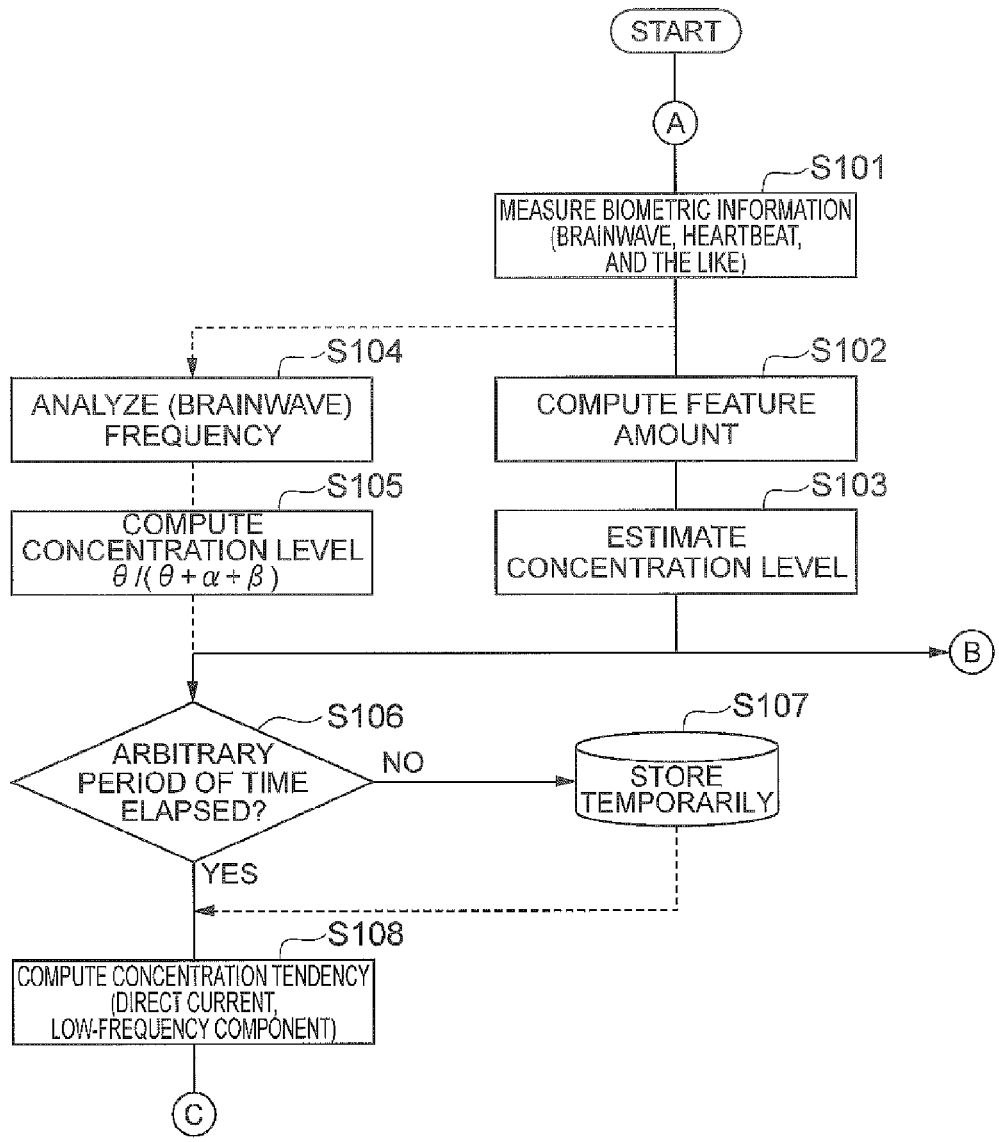
FIG. 4 is a flowchart illustrating an operation of estimating the concentration level of a driver in the driving assistance system according to the embodiment.

As illustrated in FIG. 4, the heartbeat sensor 122 mounted on a driver measures biometric information such as the heartbeat of the driver when the driver is in the vehicle or not in the vehicle (S101).

The heartbeat feature amount computing unit 130 of the portable terminal 130 that receives the heartbeat of the driver from the heartbeat sensor 122 computes, among types of data related to the heartbeat, the θ wave content ratio from the interval or fluctuation of R waves as the amount of features of the heartbeat (S102). The θ wave content ratio is computed by the equation of θ wave content ratio=θ wave power/(α wave power+β wave power+θ wave power). The concentration level computing unit 140 in the portable terminal 130 computes the concentration level of the driver from the θ wave content ratio (S103). In the present embodiment, for the purpose of correction, actually, a θ wave of the driver can be extracted through frequency analysis by the brainwave sensor 121 (S104), and the concentration level of the driver can be computed with the obtained θ wave (S105).

While an arbitrary period of time does not elapse (S106), the concentration change computing unit 152 of the concentration tendency computing unit 150 temporarily stores the concentration level of the driver that is obtained for each point in time (S107). When an arbitrary period of time elapses (S106), the concentration change computing unit 152 computes the tendency of the concentration level of the driver to decrease by extracting a direct current component or a low-frequency component from a change in the time series of the concentration level configured of the θ wave content ratio (S108).

Figure 8:
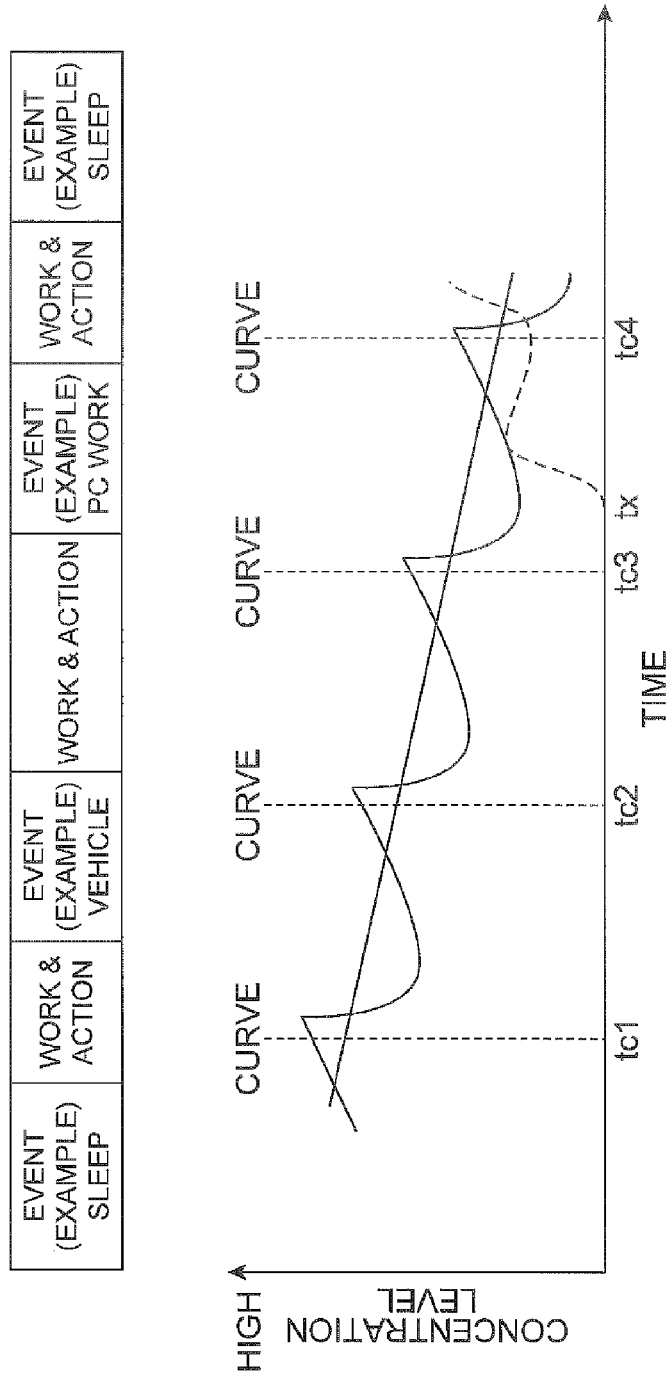
FIG. 8 is a graph illustrating a temporal decrease in the concentration level of a driver.

As illustrated in FIG. 8, it is assumed that there are events such as a sleeping, driving of the vehicle, and working with a personal computer between work and action that do not require a concentration level in an ordinary day of the driver. The concentration level of the driver decreases linearly as illustrated by a straight line in FIG. 8 during driving of the vehicle on an even road. Meanwhile, the concentration level of the driver temporarily rises at points in time tc1 to tc4 when the vehicle passes through a curve. However, the concentration level of the driver decreases over time. As illustrated by a broken line, the concentration level decreases when the driver takes a rest at a point in time tx. In the traveling thereafter, the concentration level is recovered more than when driving is continued. Therefore, it is considered that the concentration level of the driver can be maintained by prompting the driver to take an appropriate rest.

Figure 9:
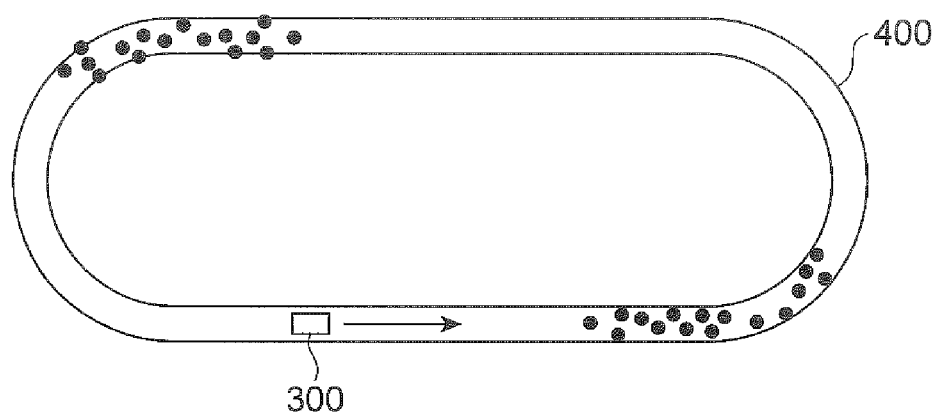
FIG. 9 is a plan view illustrating locations where the concentration level of a driver increases on a course along which a vehicle travels.
Figure 10:
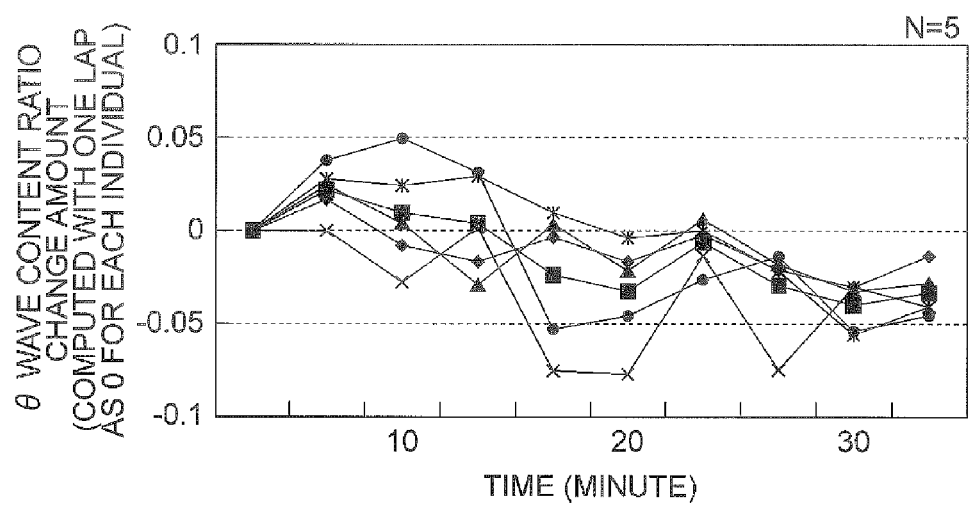
FIG. 10 is a graph illustrating the amount of change of a $\theta$ wave content ratio with respect to the number of laps of a course for each driver.
Figure 11:
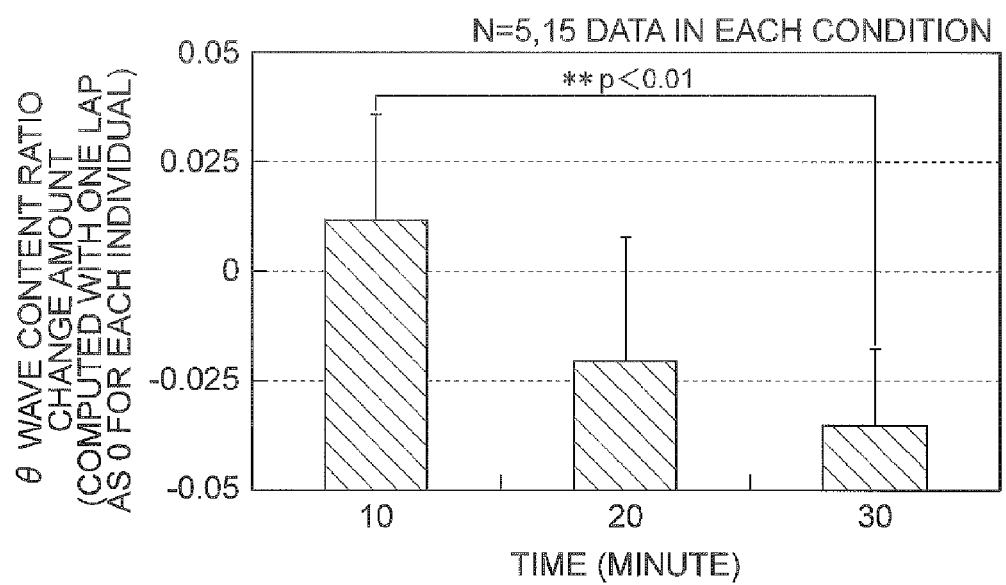
FIG. 11 is a graph illustrating the amount of change of a $\theta$ wave content ratio of a driver with respect to the number of laps of a course that is assumed to be a highway.

As illustrated in FIG. 9, when a vehicle 300 travels a lap of a course 400, it is determined that the concentration level increases immediately before curves as illustrated by black points in FIG. 9. As illustrated in FIG. 10, it is determined that the θ wave content ratios of five drivers decrease similarly although varying from each other for each period of time. As illustrated in FIG. 11, it is determined that a change in concentration level for every 10 minutes also decreases on an assumed highway.

The concentration change computing unit 152, therefore, can estimate the tendency of the concentration level of the driver to decrease by measuring the period of time until the concentration level reaches an arbitrary concentration level. Alternatively, the concentration change computing unit 152 can predict the tendency of the concentration level to decrease from the direct current component of the concentration level in an arbitrary section. The concentration change computing unit 152 can predict a driver-specific tendency of the concentration level to decrease from the direct current component of the concentration level. In addition, the concentration change computing unit 152 can predict the tendency of the concentration level to decrease due to the condition of the driver in a day from the direct current component of the concentration level. In addition, the concentration change computing unit 152 can predict the period of time until the concentration level drops to an arbitrary threshold from the tendency of the concentration level to decrease.

Specifically, the concentration change computing unit 152 measures the concentration level from when driving starts or when the vehicle passes through the entrance of the highway. The concentration change computing unit 152 computes the average concentration level from the initiation of the measurement for five minutes. The concentration change computing unit 152 then can compute the average concentration level for every five minutes or 10 minutes and can compute the proportion of attenuation of the concentration level from the differences.

The concentration change computing unit 152 computes with a linear equation the period of time until the θ wave content ratio reaches an arbitrary threshold from an initial concentration level, in which the arbitrary threshold is, for example, 0.54 which is a statistical value. As will be described below, the display device 210 reports a decrease in the concentration level to the driver 15 minutes prior to the time when the θ wave content ratio reaches an arbitrary threshold. The concentration change computing unit 152 can accumulate data for a long period of time for each driver and can compute a straight line or a curve other than a straight line that indicates the tendency of the concentration level to decrease from least squares of the data.

Figure 12:
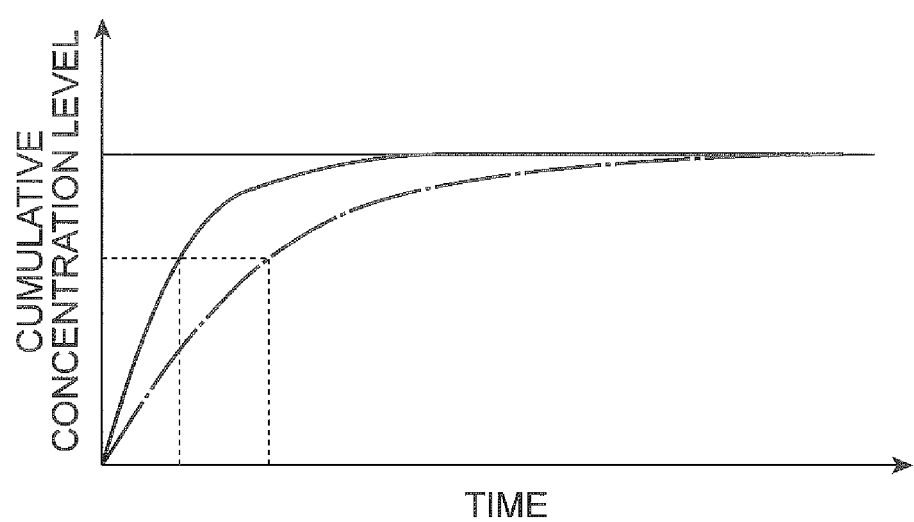
FIG. 12 is a graph illustrating the concept of a temporal change in a cumulative concentration level.
Figure 13:
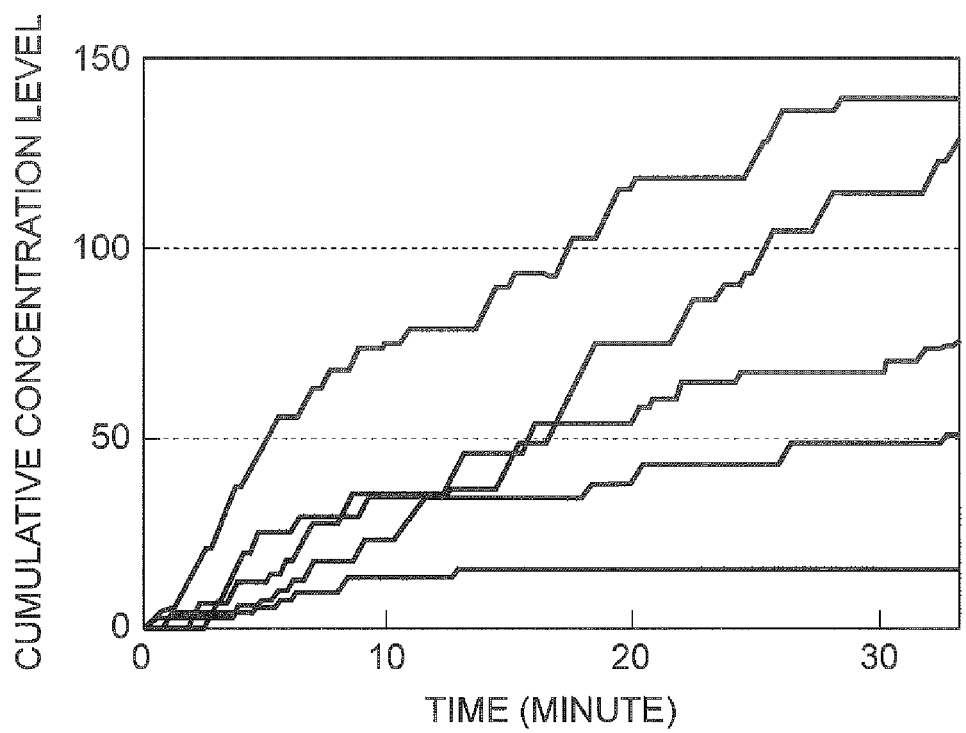
FIG. 13 is a graph illustrating a measured value of a cumulative concentration level with respect to time corresponding to the number of laps of a course.

In the present embodiment, the time constant computing unit 154 of the concentration tendency computing unit 150 can compute the period of time until the degree of fatigue of the driver or the degree of accumulation of the concentration level of the driver is saturated from the period of time until the degree of accumulation of the concentration level reaches an arbitrary threshold. As illustrated in FIG. 12 and FIG. 13, the cumulative amount of the concentration level of the driver over time is saturated after a certain period of time like a temporary delay. Thus, the time constant computing unit 154 can compute a time constant from the cumulative amount of the concentration level. The time constant computing unit 154 can compute a time limit within which the driver can concentrate or the degree of fatigue of the driver from the time constant.

The time constant computing unit 154 measures the concentration level from when driving starts or when the vehicle passes through the entrance of the highway. The time constant computing unit 154 classifies the θ wave content ratio with an arbitrary threshold, for example, 0.65. The time constant computing unit 154 defines the case where the θ wave content ratio is greater than or equal to the threshold as 1, defines the case where the θ wave content ratio is less than the threshold as 0, and obtains the cumulative concentration level for each unit time.

The time constant computing unit 154 measures the time when the cumulative concentration level of the driver reaches an arbitrary value and computes the time constant from the measured time. The time constant computing unit 154 computes the period of time until the cumulative concentration level is saturated from the time constant. The time constant computing unit 154, when the value of the added cumulative concentration level is below 1, may compute the time constant from the period of time thereuntil and may compute the period of time until the cumulative concentration level is saturated.

In the present embodiment, since accumulation is performed with binary classification so as to obtain the time constant, the period of time until the cumulative amount of the concentration level is saturated can be computed independently of the accuracy of the data.

Figure 5:
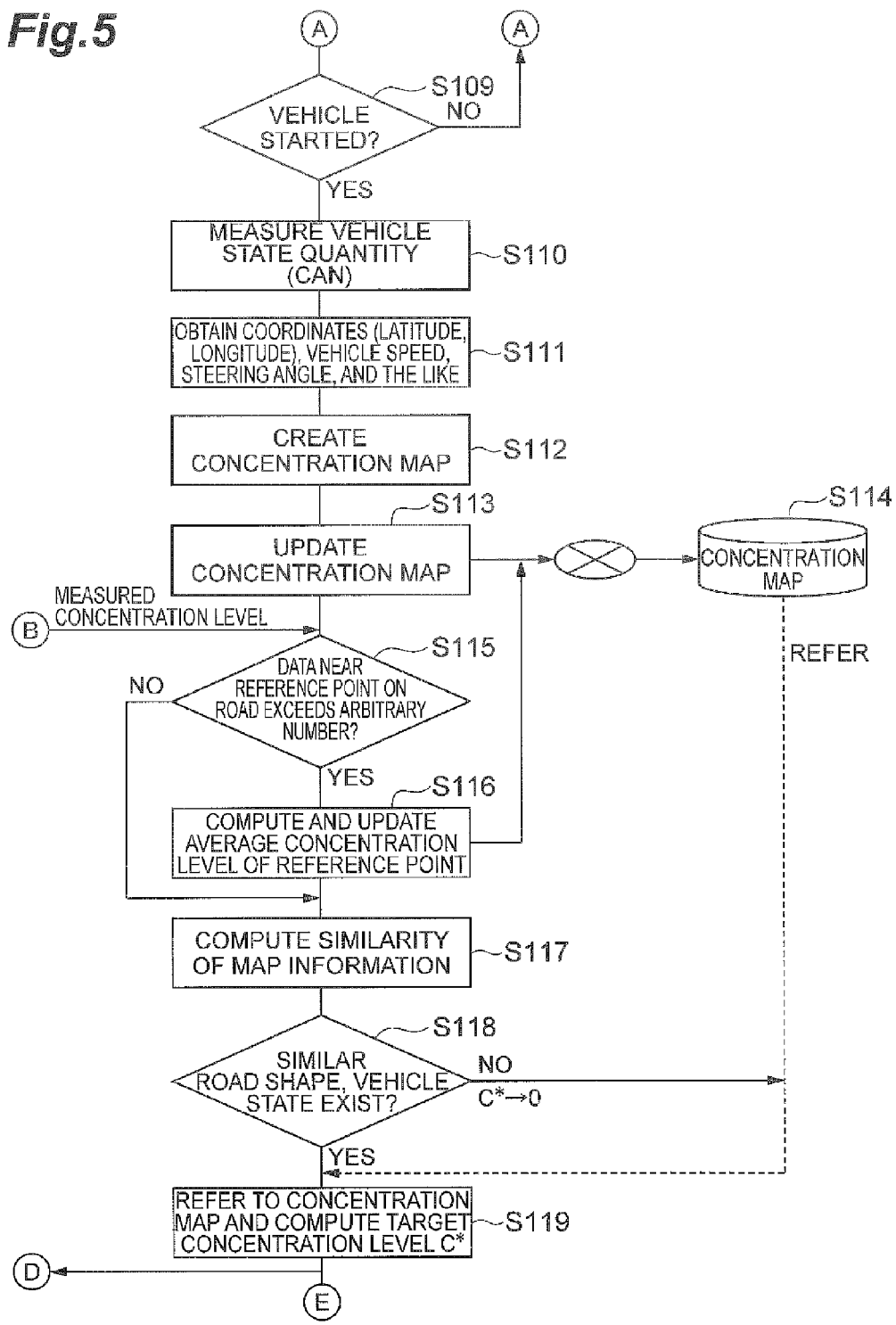
FIG. 5 is a flowchart illustrating an operation of creating a concentration map and computing an on-road target concentration level in the driving assistance system according to the embodiment.

As illustrated in FIG. 5, when the driver enters the vehicle and starts the vehicle (S109), the vehicle information detecting unit 110 and the feature amount computing unit 112 obtain, from the GPS, the navigation system, and the CAN, positional information such as the latitude and the longitude of the road that the vehicle currently travels or the road that is predicted to be traveled by the vehicle in the future, time, the vehicle speed, the degree to which the accelerator is opened, a braking signal, the yaw rate, the steering angle, and the like (S110 and S111). At this time, as described above, the concentration level is computed from the θ wave content ratio of the driver in the concentration level computing unit 140. The concentration map computing unit 114 computes the concentration map on which the positional information of the vehicle and information such as the vehicle speed are recorded after being correlated with the concentration level (S112 and S113). By doing as such, the concentration map can be simply created independently of multivariate environmental information related to the road. In addition, influence of locations and time on the concentration level can be easily perceived. In this case, the curvature, the width, the gradient, the speed limit, the amount of traffic, and the like of the road recorded on the map data of the navigation system may be recorded after being correlated with the concentration level.

The concentration map computing unit 140 updates the concentration map stored on the server 175 through the network 170 (S113 and S114). Reference points having reference coordinates are prepared for each certain section in the map data of the navigation system. When a certain amount of learning data is accumulated (S115), the concentration map computing unit 140 updates the concentration map by obtaining the average value of the data on the basis of the data in the case where data related to a latitude and a longitude near the reference point exceeds an arbitrary number, for example, 50 (S116).

Figure 14:
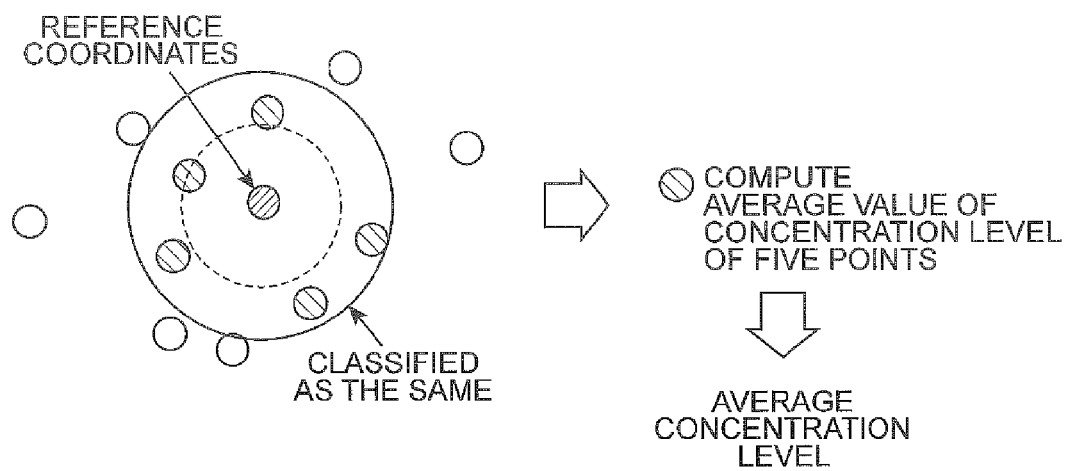
FIG. 14 is a diagram illustrating a manner of creating the concentration map of the embodiment.

It is assumed that, for example, the concentration map is updated when five pieces of data are collected. As illustrated in FIG. 14, it is assumed that there are obtained five pieces of data that are related to the concentration level and are illustrated by black points within a certain distance from the reference coordinates. In this case, the concentration map computing unit 140 computes the average value of the five points of the concentration levels and updates the concentration level of the reference coordinates as the average value. Similarly, the concentration map computing unit 140 updates the concentration map again each time the data near the reference coordinates is increased as 50, 100, and 150.

The state determining unit 160, when the shape, the gradient, the curvature, the speed limit, the amount of traffic, and the like of the road that the vehicle currently travels or the road that the vehicle is supposed to travel are the same as or similar to the shape and the like of the road recorded on the concentration map (S118), computes a target concentration level C* by referring to the concentration map (S119). The target concentration level C* can be set as the concentration level that is the same as or higher by a predetermined margin than the concentration level of each of the reference coordinates recorded on the concentration map. Accordingly, the target concentration level C* can be computed even on a road that the vehicle travels for the first time.

Figure 6:
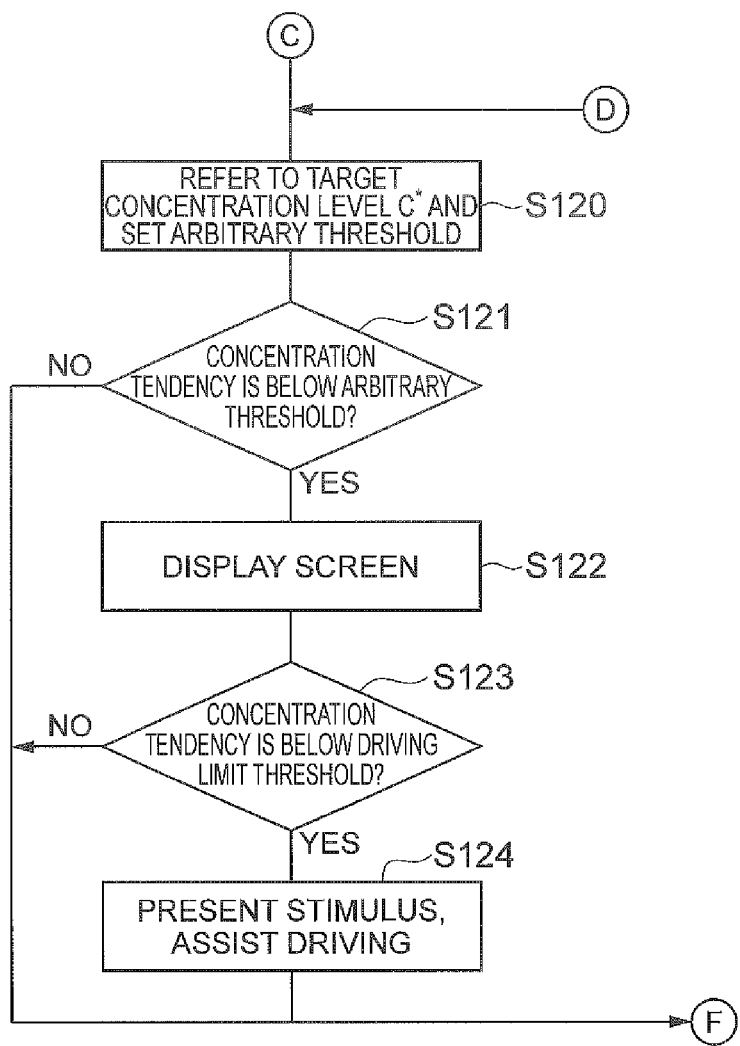
FIG. 6 is a flowchart illustrating an operation of performing driving assistance through a comparison of a concentration tendency of a driver with a threshold based on a target concentration level in the driving assistance system according to the embodiment.

As illustrated in FIG. 6, the state determining unit 160 refers to the target concentration level C* computed from the concentration map and sets an arbitrary threshold (S120). This arbitrary threshold may be the same value as the target concentration level C*, may be a value higher by a predetermined value than the target concentration level C*, or may be a value lower by a predetermined value than the target concentration level C*. The arbitrary threshold in this case is set as a higher value than a lower limit of the concentration level that is required for the driver to drive on the road which is predicted to be traveled by the vehicle.

The state determining unit 160 compares the concentration level that is required on the road which is predicted to be traveled by the vehicle with the future concentration level of the driver. Regarding the tendency of the concentration level of the driver to decrease over time, which is estimated by the concentration tendency computing unit 150, the state determining unit 160 determines whether the concentration level of the driver is below an arbitrary threshold after an arbitrary period of time (S121). For example, when the concentration level of the driver is below an arbitrary threshold after 15 minutes (S121), the display device 210 plays a video or a sound to call attention of the driver about a decrease in the concentration level and displays the most recent route traveled for a rest to a service area or a parking area, a guide to rest facilities, and advertisements such as information, products, and the like of stores in the resting facilities (S122).

Regarding the tendency of the concentration level of the driver to decrease over time, which is estimated by the concentration tendency computing unit 150, the state determining unit 160 determines whether the concentration level of the driver is below the threshold that is the lower limit of the concentration level required for driving after an arbitrary period of time (S123). In this case, the threshold that is the lower limit of the concentration level required for driving, as described above, can be set as the concentration level when the degree of accumulation of the concentration level of the driver is saturated. In addition, the arbitrary period of time is set as a period of time during which the driver can drive the vehicle safely.

When the concentration level of the driver is below the threshold that is the lower limit of the concentration level required for driving after an arbitrary period of time (S123), the assistance device 220 first performs driving assistance in which the vehicle travels at a constant speed and follows another vehicle independently of a driving operation by the driver and reduces load of a vehicle speed control on the driver (S124). When the concentration level does not rise even after a predetermined period of time elapses (S101 to S123), the assistance device 220 performs driving assistance of maintaining the lane traveled by the vehicle independently of a driving operation by the driver, and in the meantime, the display device 210 prompts the driver to take a rest in a service area or a parking area (S124). When there is no change in the driving operation by the driver even after a predetermined period of time elapses, the assistance device 220 may forcibly intervene in the driving operation by the driver and guide the method of traveling of the vehicle. In addition, the assistance device 220, when the vehicle has a possibility of contacting an obstacle until reaching the place where the driver can take a rest, can perform driving assistance for avoiding contact or reducing damage of the contact. Driving assistance for avoiding contact or reducing damage of the contact includes avoiding contact by intervening in a braking operation by the driver and avoiding contact by intervening in a steering operation by the driver. In addition, the display device 210 can perform driving assistance for avoiding contact or reducing damage of the contact by calling attention of the driver to the obstacle. Alternatively, if necessary, the assistance device 220 can perform driving assistance for stabilizing traveling of the vehicle.

The display device 210 and the assistance device 220 can determine the content of driving assistance depending on the position or the environment in which the vehicle travels. For example, when the vehicle travels along a curve, the assistance device 220 can perform driving assistance of maintaining the lane traveled by the vehicle independently of a driving operation by the driver. For example, when the vehicle travels a corner that has a blind spot, the display device 210 can display the blind spot. When the display device 210 performs driving assistance for the driver, the display device 210 can perform any of displaying a captured image of the area around the vehicle and prompting the driver to see a direction around the vehicle.

The above operations of S101 to S108 and S120 to S124 can be performed in an aspect of displaying whether the concentration level of the driver is sufficient for driving of the vehicle on the portable terminal 130 even when the driver is not in the vehicle.

Figure 7:
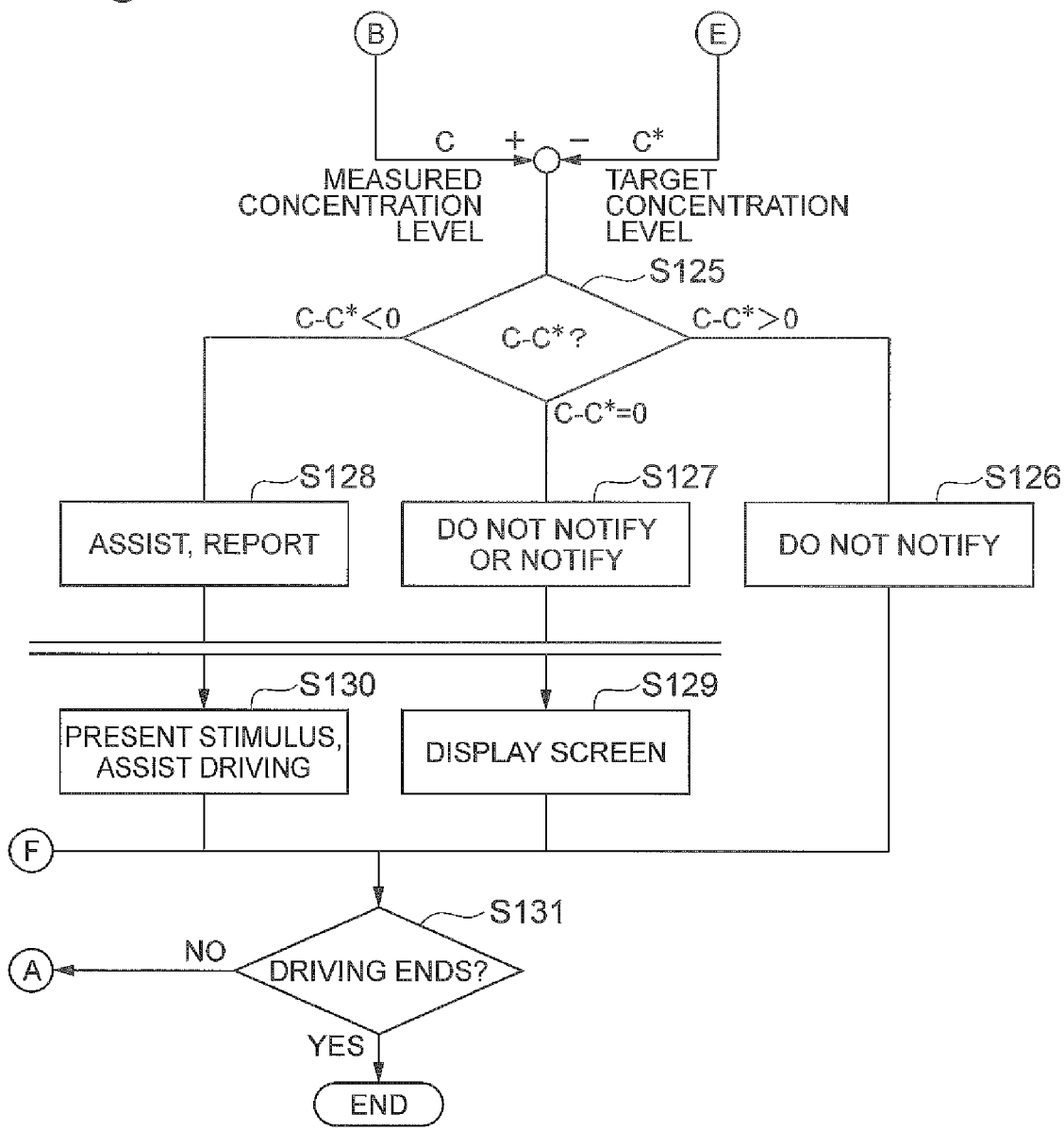
FIG. 7 is a flowchart illustrating an operation of performing driving assistance through a comparison of a target concentration level with a measured concentration level in the driving assistance system according to the embodiment.

The state determining unit 160 compares the concentration level that is required on the road which the vehicle currently travels with the current concentration level of the driver. As illustrated in FIG. 7, the state determining unit 160 compares a concentration level C of the driver that is currently measured and computed by the concentration level computing unit 140 with the above target concentration level C* that is required on the road which the vehicle currently travels (S125).

When the concentration level C measured is higher than the target concentration level C* (S125), the display device 210 does not perform displaying (S126). When the concentration level C measured is the same as the target concentration level C*, the display device 210 may perform displaying as described in S122 or may not perform displaying (S127 and S129). When the concentration level C measured is lower than the target concentration level C* (S125), the display device 210 and the assistance device 220 perform displaying and driving assistance as described in S122 and S124 (S128 to S130). The above operations of S109 to S130 are continued until driving of the vehicle ends (S131).

According to the present embodiment, the heartbeat sensor 122 obtains the heartbeat of the driver. The concentration level computing unit 140 estimates the concentration level of the driver at a time later than the timing of obtaining the heartbeat by the heartbeat sensor 122, on the basis of the heartbeat obtained by the heartbeat sensor 122. The state determining unit 160 controls driving assistance for the vehicle on the basis of the comparison of the concentration level of the driver estimated by the concentration level computing unit 140 with the target concentration level of the driver that is set in association with the position or the environment in which the vehicle driven by the driver is predicted to travel. Accordingly, current driving assistance is controlled on the basis of the comparison of the future concentration level of the driver based on the actual obtained heartbeat with the target concentration level of the driver that is obtained in the position or the environment in which the vehicle travels in the future. Thus, driving assistance is performed more appropriately for the situation in which the driver performs driving in the position or the environment, and the possibility of causing the driver to feel inconvenienced can be reduced.

The state determining unit 160 promotes driving assistance as the degree to which the concentration level of the driver estimated by the concentration level computing unit 140 does not satisfy the target concentration level of the driver that is set in association with the position or the environment in which the vehicle driven by the driver is predicted to travel is greater. Accordingly, driving assistance is promoted as the concentration level of the driver is lower in the situation in which the driver performs driving in the position or the environment. Thus, driving assistance is performed more appropriately for the concentration level of the driver and the conditions corresponding to the position or the environment, and the possibility of causing the driver to feel inconvenienced can be reduced. The "promotion of driving assistance" in the present embodiment is not limited to the promotion above through the initiation of driving assistance and includes the case where, for an obstacle which is the target of driving assistance, the obstacle is easily detected by increasing a detection range, by increasing detection accuracy, and the like. In addition, the "promotion of driving assistance" in the present embodiment includes the case where conditions for initiating driving assistance are relaxed by decreasing a threshold for initiating driving assistance. In addition, the "promotion of driving assistance" in the present embodiment includes the case where the time of initiating driving assistance is hastened. In addition, the "promotion of driving assistance" in the present embodiment includes the case where driving assistance is promoted by increasing the degree of driving assistance from simple presentation of information to reporting and intervening in the driving of the driver.

The state determining unit 160 initiates driving assistance when the concentration level of the driver estimated by the concentration level computing unit 140 does not satisfy the target concentration level of the driver that is set in association with the position or the environment in which the vehicle driven by the driver is predicted to travel. Thus, driving assistance is performed for the concentration level of the driver and the conditions corresponding to the position or the environment when necessary, and the possibility of causing the driver to feel inconvenienced can be reduced.

The concentration change computing unit 152 of the concentration tendency computing unit 150 estimates the tendency of the concentration level of the driver to decrease over time on the basis of the heartbeat obtained by the heartbeat sensor 122. Accordingly, the concentration level of the driver when the vehicle actually travels in the position or the environment can be estimated more accurately, and driving assistance can be performed more appropriately for the concentration level of the driver.

The time constant computing unit 154 of the concentration tendency computing unit 150 estimates the period of time until the degree of accumulation of the concentration level of the driver over time is saturated on the basis of the heartbeat obtained by the heartbeat sensor 122 and estimates the tendency of the concentration level of the driver to decrease over time on the basis of the period of time until the degree of accumulation is saturated. The period of time until the degree of accumulation of the concentration level of the driver over time is saturated is unlikely to be affected by temporary variation of the concentration level of the driver. Therefore, a tendency of the concentration level of the driver to decrease over time can be estimated more accurately regardless of temporary variation of the concentration level of the driver by estimating the period of time until the degree of accumulation of the concentration level of the driver over time is saturated.

The state determining unit 160, on the basis of the heartbeat obtained by the heartbeat sensor 122, associates the concentration level of the driver at the timing of obtaining biometric information by the heartbeat sensor 122 with the position or the environment in which the vehicle driven by the driver travels and records the association. Accordingly, the concentration level of the driver when the vehicle travels in the position or the environment can be correlated with the position or the environment.

The target concentration level of the driver that is set in association with any of the position and the environment in which the vehicle driven by the driver is predicted to travel is set on the basis of the concentration level of the driver that is recorded after being associated with the position or the environment in which the vehicle driven by the driver travels. Therefore, the target concentration level of the driver corresponds to the concentration level of the driver when the vehicle travels in the position or the environment, and conditions can be set more realistically.

The display device 210 and the assistance device 220 perform driving assistance that is set in association with the position or the environment in which the vehicle driven by the driver is predicted to travel. Thus, it is possible to perform driving assistance that is more appropriate for the position or the environment in which the vehicle travels.

The display device 210 calls to the attention of the driver when the state of the driver estimated by the concentration level computing unit 140 is below an arbitrary threshold. The assistance device 220 performs driving assistance of intervening in a driving operation by the driver when the state of the driver estimated by the concentration level computing unit 140 is below the lower limit of the concentration level that is lower than an arbitrary threshold. Accordingly, the concentration level that is required for the driver to drive the vehicle can be reduced. In addition, an inconvenient feeling of the driver can be reduced because assistance that the driver needs is provided.

The heartbeat sensor 122 obtains the heartbeat of the driver. The concentration level computing unit 140 estimates the concentration level of the driver at a time later than the timing of obtaining the heartbeat by the heartbeat sensor 122, on the basis of the heartbeat obtained by the heartbeat sensor 122. The display device 210 selects a course to guide the driver from multiple courses on the basis of the comparison of the concentration level of the driver estimated by the concentration level computing unit 140 with the target concentration level of the driver that is set in association with the position or the environment in which the vehicle driven by the driver is predicted to travel in the multiple courses. Accordingly, the course to be guided to the driver is selected on the basis of the comparison of the future concentration level of the driver based on the actual obtained heartbeat with the target concentration level of the driver obtained in the position or the environment in which the vehicle is predicted to travel in the future in the multiple courses. Thus, the course that is more appropriately for the situation in which the driver performs driving in the position or the environment is guided, and the possibility of causing the driver to feel inconvenienced can be reduced.

The present invention is not limited to the embodiment above and is able to be modified in various manners. The period of time of computing the concentration level is not limited to five minutes or 10 minutes and may be an arbitrary period of time. The direct current component in the computation of the concentration level may be represented by a non-linear function such as an exponential function. In addition, in the above embodiment, the information-providing device of the present embodiment is mainly described as being applied to a vehicle. However, in the present embodiment, for example, the display device 210 can be set as a display of a personal computer. In this case, as described above, the display displays the concentration level 214 only when the concentration level of the subject decreased during work with the personal computer and notifies the subject of a decrease in the concentration level. When the concentration level is below a predetermined threshold, the display can present suggestions and the like of work other than work with the display or less burdening monotonous work to the subject.

Driving assistance for the driver performed by the driving assistance device 200 is not limited to the aspect in which the state where driving assistance such as reporting of warning is not performed at all is transitioned to the state where driving assistance such as reporting of warning is performed. The present embodiment includes the aspect in which the state where driving assistance such as reporting of warning is performed is switched to the state where different driving assistance such as intervention in the driving of the driver is performed. In addition, the present embodiment includes the aspect in which the state where driving assistance such as reporting of warning is performed is transitioned to the state where different driving assistance such as intervention in the driving of the driver is performed in addition to warning.

INDUSTRIAL APPLICABILITY

According to the driving assistance device, the driving assistance method, the information-providing device, the information-providing method, the navigation device, and the navigation method of one embodiment of the present invention, a driver feels less inconvenienced by performing driving assistance that is more appropriate for a situation where a vehicle is traveling.

REFERENCE SIGNS LIST

10 DRIVING ASSISTANCE SYSTEM
11 BIOMETRIC INFORMATION DETECTING UNIT
12 CONCENTRATION LEVEL COMPUTING UNIT
13 VEHICLE INFORMATION DETECTING UNIT
14 CONCENTRATION TENDENCY COMPUTING UNIT
15 CONCENTRATION MAP COMPUTING UNIT
16 STATE DETERMINING UNIT
17 STIMULUS PRESENTATION UNIT
18 INFORMATION-PROVIDING UNIT
100 STATE ESTIMATION SYSTEM
110 VEHICLE INFORMATION DETECTING UNIT
112 FEATURE AMOUNT COMPUTING UNIT
114 CONCENTRATION MAP COMPUTING UNIT
115 ON-BOARD DEVICE
120 BIOMETRIC INFORMATION DETECTING UNIT
121 BRAINWAVE SENSOR
122 HEARTBEAT SENSOR
123 PUPIL SENSOR
130 PORTABLE TERMINAL
131 BRAINWAVE FEATURE AMOUNT COMPUTING UNIT
132 HEARTBEAT FEATURE AMOUNT COMPUTING UNIT
133 PUPIL FEATURE AMOUNT COMPUTING UNIT
140 CONCENTRATION LEVEL COMPUTING UNIT
150 CONCENTRATION TENDENCY COMPUTING UNIT
152 CONCENTRATION CHANGE COMPUTING UNIT
154 TIME CONSTANT COMPUTING UNIT
160 STATE ESTIMATING UNIT
170 NETWORK
175 SERVER
200 DRIVING ASSISTANCE DEVICE
210 DISPLAY DEVICE
212 MAP
214 CONCENTRATION POWER
300 VEHICLE
400 COURSE

The invention claimed is:

1. A driving assistance device comprising:
a biometric information obtaining unit configured to obtain biometric information of a driver;
a driver state estimating unit configured to estimate, on the basis of the biometric information obtained by the biometric information obtaining unit, a state of the driver at a time later than a timing of obtaining the biometric information by the biometric information obtaining unit; and
a control unit configured to control driving assistance of a vehicle on the basis of a comparison of the state of the driver estimated by the driver state estimating unit with a condition for the state of the driver that is set in association with any one of a position and an environment in which the vehicle driven by the driver is predicted to travel,
wherein the state of the driver is a concentration level of the driver;
wherein the driver state estimating unit, on the basis of the biometric information obtained by the biometric information obtaining unit, estimates a tendency of the concentration level of the driver to decrease over time; and
wherein the control unit promotes the driving assistance as a degree to which the state of the driver estimated by the driver state estimating unit does not satisfy the condition for the state of the driver that is set in association with any one of the position and the environment in which the vehicle driven by the driver is predicted to travel is greater.

2. The driving assistance device according to claim 1, wherein the control unit controls the driving assistance to be initiated when the state of the driver estimated by the driver state estimating unit does not satisfy the condition for the state of the driver that is set in association with any one of the position and the environment in which the vehicle driven by the driver is predicted to travel.

3. The driving assistance device according to claim 1, wherein the driver state estimating unit, on the basis of the biometric information obtained by the biometric information obtaining unit, estimates a tendency of the concentration level of the driver to decrease over time by estimating a degree of accumulation of the concentration level of the driver over time.

4. The driving assistance device according to claim 3, wherein the driver state estimating unit, on the basis of the biometric information obtained by the biometric information obtaining unit, estimates a period of time until the degree of accumulation of the concentration level of the driver over time is saturated and estimates a tendency of the concentration level of the driver to decrease over time on the basis of the time period until the degree of accumulation is saturated.

5. The driving assistance device according to claim 1, wherein the control unit, on the basis of the biometric information obtained by the biometric information obtaining unit, associates the state of the driver estimated at the timing of obtaining the biometric information by the biometric information obtaining unit with any one of the position and the environment in which the vehicle driven by the driver travels and records the association.

6. The driving assistance device according to claim 5, wherein the condition for the state of the driver that is set in association with any one of the position and the environment in which the vehicle driven by the driver is predicted to travel is set on the basis of the state of the driver that is recorded in association with any one of the position and the environment in which the vehicle driven by the driver travels.

7. The driving assistance device according to claim 1, wherein the control unit performs the driving assistance that is set in association with any one of the position and the environment in which the vehicle driven by the driver is predicted to travel.

8. The driving assistance device according to claim 1, wherein the control unit calls to the attention of the driver when the state of the driver estimated by the driver state estimating unit is below a first threshold and performs the driving assistance of intervening in a driving operation by the driver when the state of the driver estimated by the driver state estimating unit is below a second threshold that is lower than the first threshold.

* * * * *